(12) United States Patent
Wolfberg et al.

(10) Patent No.: US 7,949,389 B2
(45) Date of Patent: May 24, 2011

(54) FETAL ECG MONITORING

(75) Inventors: Adam J. Wolfberg, Newton, MA (US); Gari D. Clifford, Boston, MA (US); Jay Ward, Stratham, NH (US)

(73) Assignees: Tufts Medical Center, Inc., Boston, MA (US); Massachusetts Institute of Technology, Cambridge, MA (US); E-Trolz, Inc., North Andover, MA (US)

( * ) Notice: Subject to any disclaimer, the term of this patent is extended or adjusted under 35 U.S.C. 154(b) by 171 days.

(21) Appl. No.: 12/424,046

(22) Filed: Apr. 15, 2009

(65) Prior Publication Data

US 2009/0259133 A1 Oct. 15, 2009

Related U.S. Application Data

(60) Provisional application No. 61/045,055, filed on Apr. 15, 2008, provisional application No. 61/100,807, filed on Sep. 29, 2008.

(51) Int. Cl.
*A61B 5/0444* (2006.01)

(52) U.S. Cl. .................. 600/511; 600/376; 600/483

(58) Field of Classification Search ............... 600/304, 600/376, 388, 390, 393, 483, 509, 511, 516, 600/517; 607/25, 26
See application file for complete search history.

(56) References Cited

U.S. PATENT DOCUMENTS

| | | | |
|---|---|---|---|
| 3,703,168 A | 11/1972 | Frink | |
| 4,211,237 A * | 7/1980 | Nagel | 600/511 |
| 4,945,917 A | 8/1990 | Akselrod et al. | |
| 5,372,139 A | 12/1994 | Holls et al. | |
| 5,666,959 A | 9/1997 | Deans et al. | |
| 5,704,365 A | 1/1998 | Albrecht et al. | |
| 5,846,189 A | 12/1998 | Pincus | |
| 6,658,284 B1 * | 12/2003 | Rosen et al. | 600/511 |
| 7,333,850 B2 | 2/2008 | Marossero et al. | |
| 2005/0267377 A1 | 12/2005 | Marossero et al. | |
| 2006/0149597 A1 | 7/2006 | Powell et al. | |
| 2006/0241510 A1 | 10/2006 | Halperin et al. | |
| 2007/0213627 A1 * | 9/2007 | James et al. | 600/511 |
| 2007/0260151 A1 | 11/2007 | Clifford | |
| 2008/0125668 A1 | 5/2008 | Graupe et al. | |

OTHER PUBLICATIONS

Wolfberg et al. "Entropy of Fetal EKG Associated with Intrapartum Fever." New England Conference on Perinatal Research. 2007.*
Vrins et al. "Abdominal Electrodes Analysis by Statistical Processing for Fetal Electrocardiogram Extraction." Proceedings of the Second International Conference. 2004.*
Wolfberg et al. "Entropy of Fetal EKG Associated with Intrapartum Fever." SMFM Abstracts. 2007.*
Sameni et al. "Electrode Selection for Noninvasive Fetal Electrocardiogram Extraction using Mutual Information Criteria." 2006.*

(Continued)

*Primary Examiner* — Carl H Layno
*Assistant Examiner* — Eugene Wu
(74) *Attorney, Agent, or Firm* — Occhiuti Rohlicek & Tsao LLP

(57) ABSTRACT

A method for fetal monitoring includes acquiring electrical signals from a set of electrodes, for example, a set of surface electrodes applied to a maternal abdominal region. The electrical signals are analyzed, including by performing a morphological analysis of fetal electrocardiogram signals. A clinical indicator is then determined from a result of performing the morphological analysis.

28 Claims, 11 Drawing Sheets

OTHER PUBLICATIONS

Ferrario et al. "Comparison of Entropy-Based Regularity Estimators: Application to the Fetal Heart Rate Signal for the Identification of Fetal Distress." IEEE Transactions on Biomedical Engineering. 2006.*

Sameni, Reza, et al. "Model-Based Bayesian Filtering of Cardiac Contaminants from Biomedical Recordings" *Physiological Measurement*. vol. 29 (2008) pp. 595-613; DOI: 1031088/0967-3334/29/5/006.

Sameni, Reza, et al. "Multichannel Electrocardiogram Decomposition Using Periodic Component Analysis" *IEEE Transactions on Biomedical Engineering*. vol. 55 No. 8 (Aug. 2008) pp. 1935-1940.

Sameni, Reza, et al. "Noninvasive Extraction of Fetal Cardiac Signals from Maternal Abdominal Recordings." (Sep. 14, 2008) pp. 1-20.

Sameni, Reza, et al. "Thesis: Extraction of Fetal Cardiac Signals from an Array of Maternal Abdominal Recordings" Institut Polytechnique de Grenoble & Sharif University of Technology (Jul. 2008) 109 pages.

Semeni, Reza "Extraction of Fetal Cardiac Signals from an Array of Maternal Abdominal Recordings" Presentation at Grenoble INP, Grenoble, France (Jul. 7, 2008) 40 pages.

Syed, Zeeshan, et al. "Clustering and Symbolic Analysis of Cardiovascular Signals: Discovery and Visualization of Medically Relevant Patterns in Long-Term Data Using Limited Prior Knowledge" *EURASIP Journal on Advances in Signal Processing*. (vol. 2007) 16 pages.

Patent Cooperation Treaty, *Notification of Transmittal of International Search Report*, PCT/US2009/040624, mailed Jun. 5, 2009, (3 pages).

Wolfberg et al., "Entropy of Fetal EKG Associated with Intrapartum Fever", Abstract, Sep. 30-Oct. 2, 2007.

Clifford et al., "Model-based Filtering, Compression and Classification of the ECG", Int. J. Bioelectomagnetism, vol. 21(2), pp. 101-104 (2005).

Wolfberg et al., "A Comparison of Subjective and Mathematical Estimations of Fetal Heart Rate Variability", *The Journal of Maternal-Fetal & Neonatal Medicine, Informa Healthcare* http://www.informaworld.com/smpp/title~content=t713453317 (2008).

Syed et al., "Clustering and Symbolic Analysis of Cardiovascular Signals: Discovery and Visualization of Medically Relevant Patterns in Long-Term Data Using Limited Prior Knowledge", *EURASIP Journal on Advances in Signal Processing*, vol. 2007, Article ID 67938, 16 Pages, (2006).

Sameni et al., "Multichannel ECG and Noise Modeling: Application to Maternal and Fetal ECG Signals", *EURASIP Journal on Advances in Signal Processing*, vol. 2007, Article ID 43407, 14 Pages, (2006).

Syed et al., "A Framework for the Analysis of Acoustical Cardiac Signals", *IEEE* (2006).

Li et al., "Robust Heart Rate Estimation From Multiple Asynchronous Noisy Sources Using Signal Quality Indices and a Kalman Filter", *Physiol. Meas.*, vol. 29, pp. 15-32, (2008).

Vrins et al., "Electrode Selection for Non-Invasive Fetal Electrocardiogram Extraction using Mutual Information Criteria", e-mail: vrins@dice.ucl.ac.be, www.dice.ucl.ac.be/~vrins 2006.

Blumensath et al., "Blind Separation of Maternal and Fetal ECG's Using Any Number of Channels", IDCOM & Joint Research Institute for Signal and Image Processing 2007.

* cited by examiner

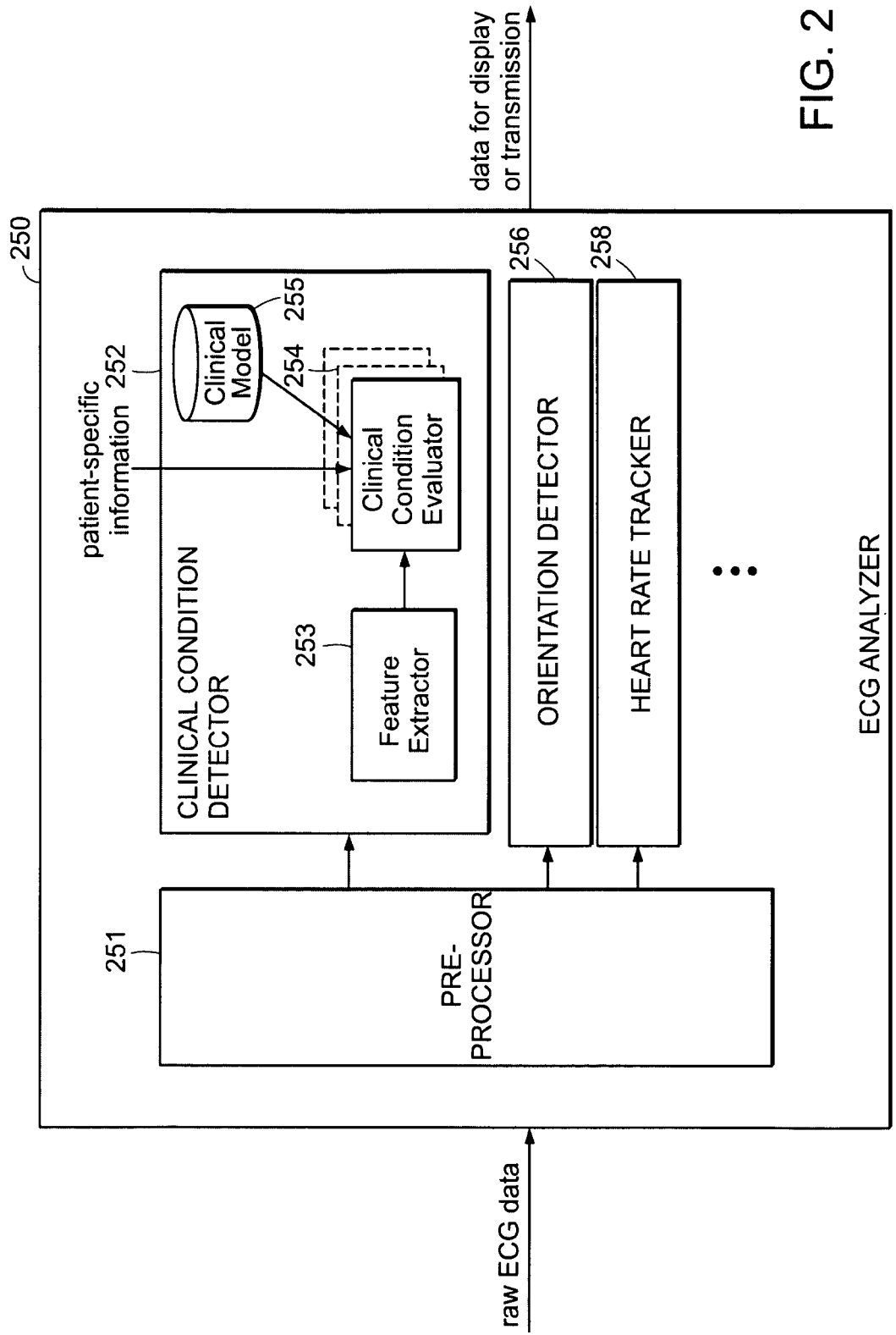

Side View
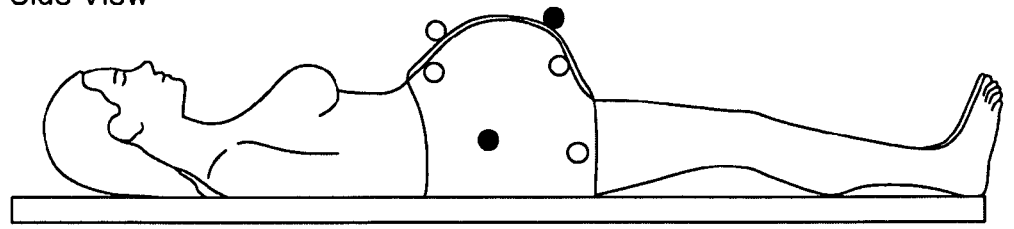
● Reference Electrode
○ Collecting Electrode
Back View
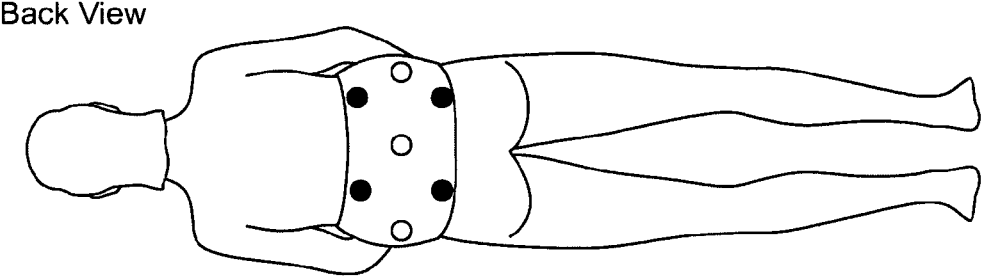
Sectional View
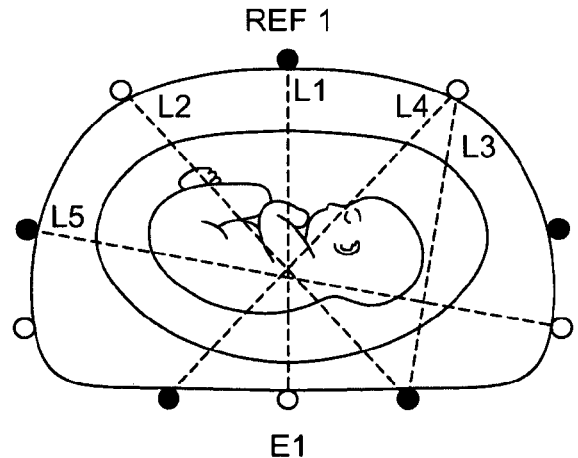
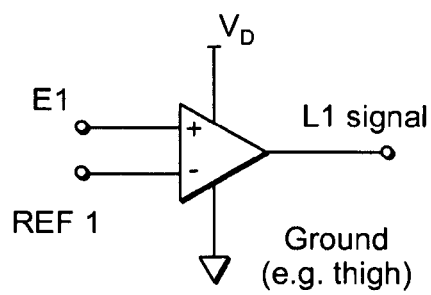
FIG. 7

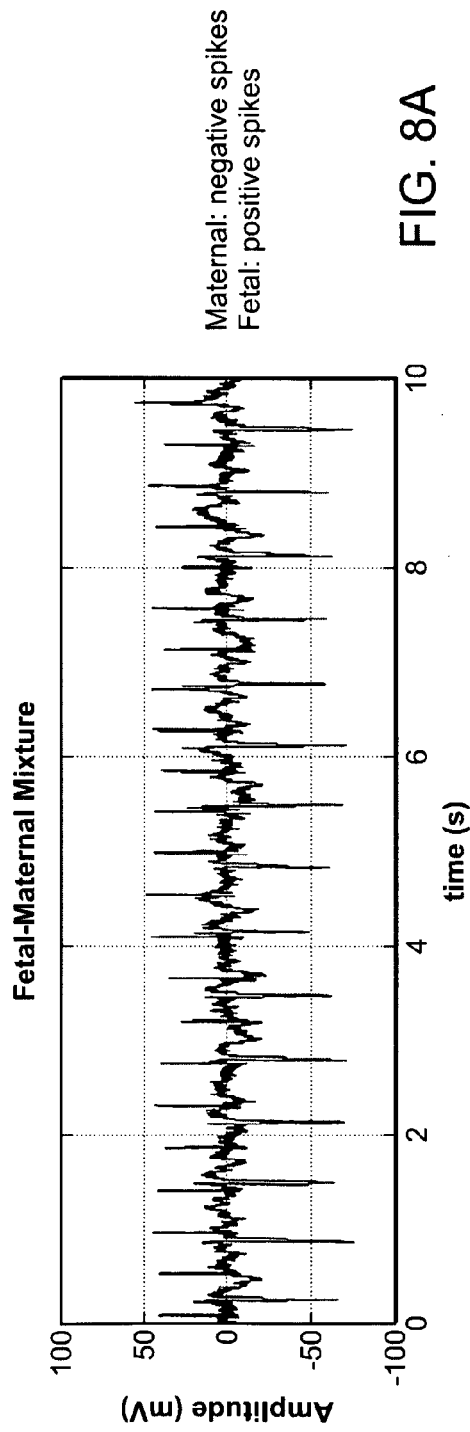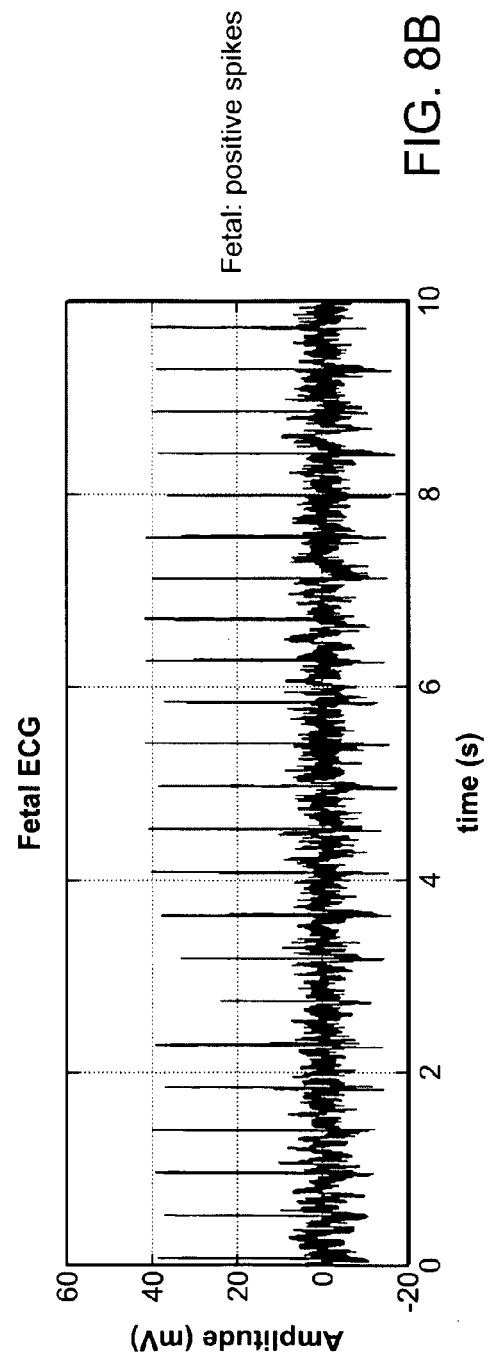

FETAL ECG MONITORING

CROSS-REFERENCE TO RELATED APPLICATIONS

This application claims the benefit of U.S. Provisional Application No. 61/045,055, titled "Fetal Monitoring System," filed Apr. 15, 2008, and U.S. Provisional Application No. 61/100,807, titled "Fetal ECG Monitoring," filed Sep. 29, 2008. The contents of the above applications are incorporated herein by references.

BACKGROUND

This specification relates to fetal ECG (fECG) monitoring.

Electrocardiogram (ECG) monitoring has been widely used on adult patients for detecting medical conditions, for example, abnormalities associated with the heart. Signals representing a patient's cardiac activities can be collected through a set of skin surface electrodes distributed over the patient's body, for example, attached to the patient's chest and limbs.

Monitoring of fetal ECG can be difficult due to the co-existence of maternal and fetal signals in raw signals acquired from a patient, as well as the relatively low fetal signal level relative to the maternal signal and other noise sources. Some conventional approaches to collecting fetal ECG signals include placing a wire electrode onto the fetal scalp. Although the fetal scalp electrode may provide a relatively clean fetal signal, this procedure can only be performed under limited clinical circumstances (e.g., when a patient is in labor, has ruptured amniotic membranes, and has a dilated cervix) and thus may not be suitable for the vast majority of pregnant and laboring patients. The placement of the fetal scalp electrode may also present certain risks to fetal safety, as rare cases of fetal scalp abscess and newborn death have been reported.

SUMMARY

In one aspect, in general, a fetal monitoring system includes a data acquisition system for acquiring signals including signals representing surface measurements of cardiac activity. A signal analyzer is coupled to the data acquisition system and is configured to analyze the acquired signals to generate an output having at least an clinical indicator characterizing a clinical condition. The signal analyzer includes a signal processor for extracting fetal electrocardiogram signals from the acquired electrical signals, and a clinical condition detector for performing a morphological analysis of the extracted fetal electrocardiogram signals, and based on a result of the morphological analysis, determining the clinical indicator. An output system is provided for presenting a representation of the clinical indicator.

Embodiments of this aspect may include one or more of the following features.

The output system includes a display unit for generating a visual representation of the output of the signal analyzer. The display unit includes, for example, a computer screen and/or a handheld device. A wireless transmitter may be provided for transmitting the output of the signal analyzer to the handheld device.

The data acquisition system includes an electrode array having at least a plurality of electrodes attachable to a maternal abdominal region. The electrode array may further include a second plurality of electrodes attachable to a maternal lumbar region, and potentially a third plurality of electrodes attachable to a maternal side region. The pluralities of electrodes are positioned in a pre-determined arrangement on a garment.

The signal analyzer further includes a heart rate detector for determining a fetal heart rate from the acquired signals. The output system is further configured for presenting a representation of the fetal heart rate determined by the signal analyzer. The heart rate detector may be further configured for determining a degree of irregularity in the fetal heart rate.

The output system is further configured for presenting a waveform representation of the fetal electrocardiogram signals.

The clinical condition detector is further configured for determining a measure of morphological variation in the extracted fetal electrocardiogram signals. The measure of morphological variation includes an entropy of a sequence of segment classifications.

The clinical indicator determined by the clinical condition detector includes an indicator of a fetal condition. The clinical indicator determined by the clinical condition detector may include an indicator of at least one of chorioamnionitis, preeclampsia, inflammation, infection, hypoxia, hypoxemia, metabolic acidosis, and fetal cardiac arrhythmias.

A signal selection unit is coupled to the signal analyzer for selectively rejecting one or more of the acquired signals based on a quality of the acquired signals.

In another aspect, in general, a fetal monitoring system includes a data acquisition system for acquiring signals including signals representing surface measurements of cardiac activity. A signal analyzer is coupled to the data acquisition system and is configured to analyze the acquired signals, including: obtaining information characterizing a fetal orientation according to a cardiac dipole model; and determining the fetal orientation based on the obtained information. An output system is provided for presenting a representation of the fetal orientation determined by the signal analyzer.

In another aspect, in general, a method for fetal monitoring includes acquiring electrical signals from a set of electrodes. These electrodes include a set of electrodes applied to a maternal abdominal region. The electrical signals are analyzed, including by performing a morphological analysis of fetal electrocardiogram signals. A clinical indicator is then determined from a result of performing the morphological analysis.

Aspects can include one or more of the following.

Performing the morphological analysis includes determining a quantitative measure of morphological variation. For example, determining the measure of morphological variation includes characterizing segments of signals determined from the acquired electrical signals according to a group of classes, and determining a measure of variation in sequences of segment classifications. The quantitative measure of morphological variation may include an entropy of a sequence of segment classifications.

Determining a clinical indicator includes determining an indicator of a fetal condition.

Determining a clinical indicator includes determining an indicator of an inflammation condition.

Determining a clinical indicator includes determining an indicator of at least one of chorioamnionitis, preeclampsia, inflammation, and infection.

In another aspect, in general, a method for fetal monitoring includes acquiring electrical signals from a plurality of electrodes. These electrodes include a plurality of electrodes applied to a maternal abdominal region. The electrical signals are analyzed, including obtaining information characterizing a fetal orientation, for example, according to a cardiac dipole model. The fetal orientation, including, for example, fetal movement and fetal position, is then determined based on the obtained information.

In another aspect, in general, a method for fetal monitoring includes acquiring electrical signals from a plurality of electrodes. These electrodes include a plurality of electrodes applied to a maternal abdominal region. The electrical signals are analyzed, including obtaining information characterizing a muscle movement associated with uterine contraction. A characteristic of the uterine contraction (e.g., a frequency or a strength the contraction) is then determined based on the obtained information.

In other aspects, in general, a medical apparatus is configured to acquiring signals from a plurality of electrodes and perform steps of the methods identified above.

In another aspect, in general, software stored on a computer readable medium includes instructions for causing a computing system to receive data representing signals from a plurality of electrodes, and perform steps of the methods described above.

Some embodiments may have one or more of the following advantages.

In some embodiments, morphologic entropy in fetal ECG signals is used as a risk metric for early detection of inflammation and neuronal injury during pregnancy, for example, due to conditions such as intrauterine infection that are associated with an increased risk of cerebral palsy and sepsis in newborns. Early detection of inflammation may allow for interventions that can reduce the risk of adverse new born outcome.

In some examples, morphologic entropy of the fetal ECG signal is measured using an unsupervised algorithm to first partition heart beats into different classes of activity based on their morphology, and then to compute the entropy of the symbolic sequence obtained by replacing each beat in the original signal with a label corresponding to its morphologic class. When evaluated on fetal ECG recordings, morphologic entropy shows a statistically significant correlation (e.g., a substantially linear association) with the level of certain biochemical marker (e.g., interleukin-8) in umbilical cord serum. This may provide a noninvasive means to detect inflammation and neuronal injury before the onset of permanent disability, thereby facilitating clinical intervention.

Other features and advantages are apparent from the following description, and from the claims.

DESCRIPTION OF DRAWINGS

FIG. 2 is a block diagram of one embodiment of the ECG analyzer of FIG. 1.

FIG. 7 shows another example of electrode configuration.

FIG. 8A shows a waveform of fetal-maternal mixture.

FIG. 8B shows a waveform of fetal ECG extracted from the fetal-maternal mixture of FIG. 8A.

DETAILED DESCRIPTION

1 Overview

Figure 1:
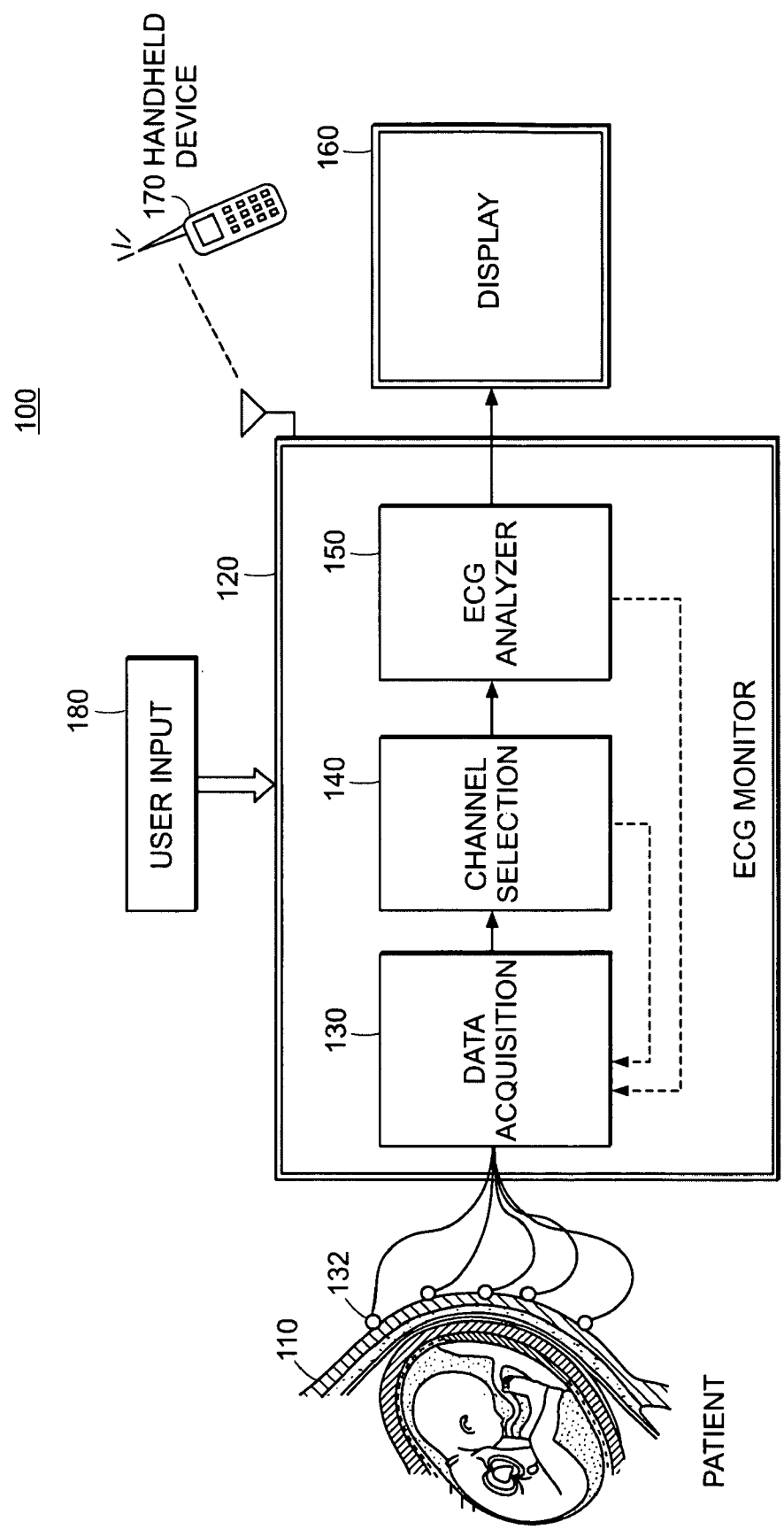
FIG. 1 is a block diagram of one embodiment of a fetal monitoring system.

Referring to FIG. 1, in some embodiments, a fetal monitoring system 100 is configured to identify characteristics of fetal ECG (fECG) signals collected from a patient 110 and based on these characteristics to detect events of clinical significance, including, for example, predicting impending fetal injury caused by inflammatory, hypoxic, or ischemic insults.

Very generally, the fetal monitoring system 100 includes an ECG monitor 120 that obtains and analyzes fetal ECG signals to generate data of clinical relevance. In some embodiments, the ECG monitor 120 makes use of morphological information in the fECG signal in addition to or instead of solely determining heart rate information. Data generated by the ECG monitor 120 can be presented to physicians in a variety of forms, for example, as printed on paper charts, shown on a display unit 160 (e.g., a computer screen), and transmitted via wireless signals to a handheld device 170 (e.g., a smart phone or PDA).

In this example, the ECG monitor 120 includes a data acquisition system 130, a channel selection module 140 (optional), and an ECG analyzer 150.

The data acquisition system 130 collects electrical signals, for example, electric potentials in the form of fetal-maternal mixtures, through a set of electrodes 132. These electrodes 132 include a set of electrodes distributed over the maternal abdomen, lower back, and/or sides, from which one or more leads are formed to generate electrical signals.

In this description, a lead is generally defined in association with a combination (e.g., a pair) of electrodes, which can be associated with an imaginary line in the body along which electrical signals are measured. A lead records the electrical signals produced by the heart (e.g., in the form of a voltage differential) from the corresponding combination of electrodes placed at specific points on the patient's body. Two different leads may use one or more common electrodes and therefore the number of leads in an ECG system is not necessarily in direct proportion to the number of electrodes placed on the patient's body. In some examples, the electrodes 132 are placed relatively far away from the maternal heart to reduce the influence of maternal signal in the fetal-maternal mixtures. In some other examples, the electrodes 132 may also include one or more electrodes placed on the maternal chest near the heart from which a maternal reference lead can be determined. The arrangement of the electrodes on the patient's body and the definition of lead pattern are selected depending on the particular implementation, as is discussed later is this document.

The signals collected by the data acquisition system 130 are transmitted to an ECG analyzer 150 that first digitizes raw ECG signals (e.g., at a sampling rate of 1,000 Hz and a resolution of 16 bits) for subsequent processing and analysis. In some examples, the raw signals are transmitted over multiple independent channels, for example, each channel for a different lead. In this example, a channel selection module 140 applies a channel selection algorithm that can discard certain channels of "weak" (low quality) signals to allow only "strong" (high quality) signals to be passed to the ECG analyzer 150. Some of the discarded channels contain primarily noise, for example, due to fetal position change or poor electrode conductivity (e.g., caused by the non-conductive gel used in an earlier ultrasound procedure). These channels are preferably rejected as the noise characteristics may not be amendable to the type of filtering technique designed for the system. Further discussion of the channel selection algorithm is provided in a later section.

Referring to FIG. 2, to obtain data of clinical significance from raw ECG signals, some embodiments of an ECG analyzer 250 include a pre-processor 251 that applies one or more filtering techniques (as will be discussed later) to generate processed ECG signals, for example, in the form of "clean" fetal ECG waveforms or metrics (i.e., parameters) of fetal-maternal ECG models. These processed signals are used by one or more analyzing modules, as described below.

1.1 Clinical Condition Detector

One example of a type of an analyzing module is a clinical condition detector 252. Very generally, the clinical condition detector 252 includes a feature extractor 253 for extracting characteristics of the ECG signals, such as heart rate variability, ECG morphology, and morphology classification and entropy, to assist clinical evaluation. These characteristics are then provided to a clinical condition evaluator 254, which identifies specific ECG patterns that are correlated with events of clinical significance. For example, the clinical condition evaluator 254 may use a clinical model 255 to correlate electrophysiological behaviors (e.g., ECG patterns) of the fetus and/or the mother with statistical behaviors in large populations associated well-established medical conditions, such as chorioamnionitis, histopathologic chorioamnionitis, and clinical neonatal infection. The resulting correlation is used to determine the susceptibility of the patient (mother and/or fetus) to such conditions. Depending on the particular implementation, the clinical condition evaluator 254 may have separate modules (e.g., a chorioamnionitis evaluator, an intrapartum fever evaluator), with each module providing a measure of a degree of the presence of a particular aspect of fetal and/or maternal distress. Physicians may receive the outputs of the individual modules in confidence scores, for example, presented on a scale of 0 to 10 with "0" indicating no (or least) distress and "10" indicating the highest level of distress. The individual scores can also be combined to form an evaluation of overall fetal distress level indicating the general health condition of the fetus.

In some embodiments, the clinical condition evaluator 254 performs an automated diagnosis to identify medical conditions (e.g., using expert systems and/or human intervention) and/or to provide recommendation for follow-up procedures. In some examples, other clinical data (such as pathologic evaluations of serum samples from the umbilical cord) are collected from the patient in pregnancy or during labor and are used by the clinical condition evaluator 254 in conjunction with the identified ECG characteristics to help further determine the likelihood of impending fetal/neonatal injuries (such as brain injuries, cerebral palsy, and death).

Using the feature extractor 253, high quality fetal ECG data can be obtained from the patient under a variety of clinical conditions (e.g., pregnant or in-labor). The characteristics of the ECG data can be well preserved to enable clinical analysis that is otherwise unavailable using conventional techniques. Implementations of the feature extractor 253 and examples of clinical condition evaluator 254 are described in greater detail at a later section.

1.2 Fetal Orientation Detector

A second example of an analyzing module is a fetal orientation detector 256 that provides an estimate of fetal position within the mother.

Figure 3C:
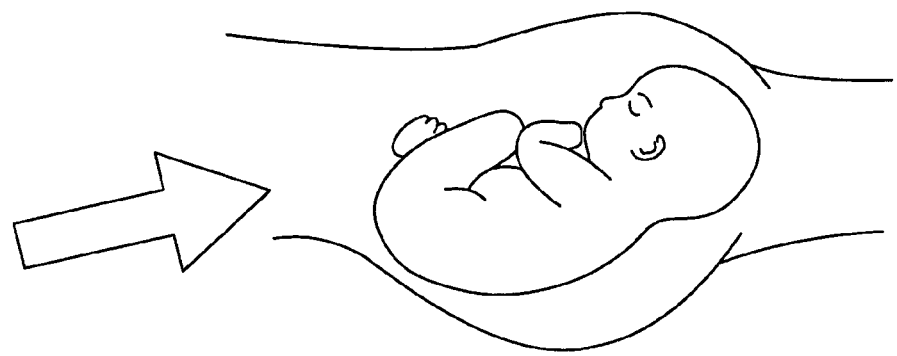
FIGS. 3A-3C illustrate fetal position changes during pregnancy.
Figure 3B:
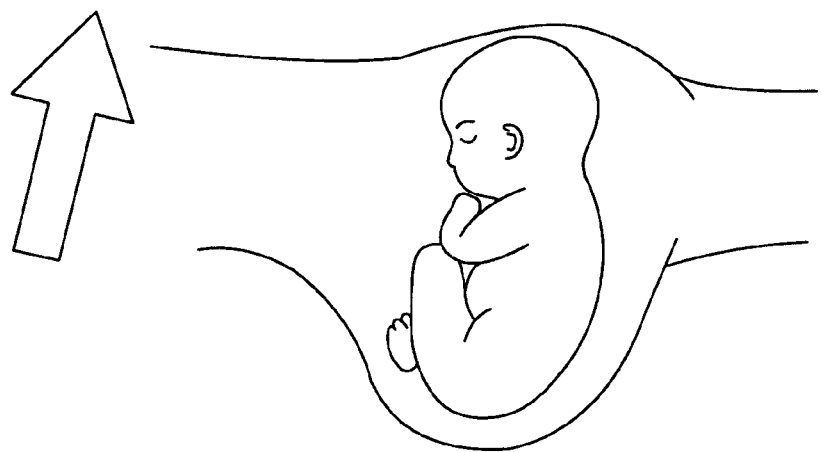
Figure 3A:
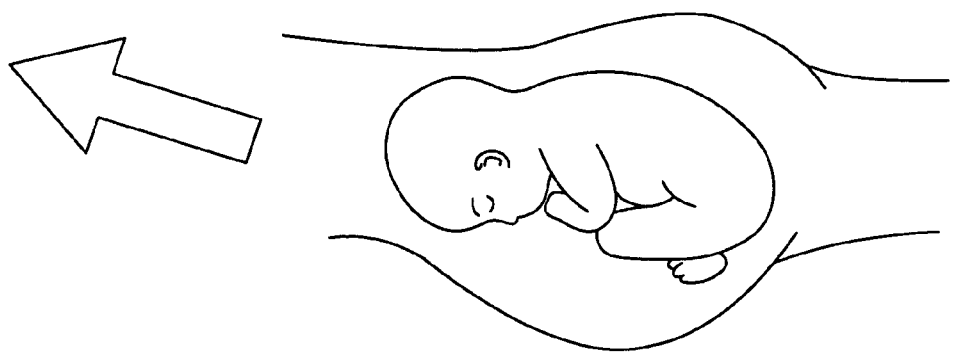

Referring to FIGS. 3A-3C, fetal position may change during various stages of pregnancy and the pre-labor position can affect the way by which the mother will deliver and whether certain cautionary steps need to be taken. In some applications, it is desirable to generate an estimate of fetal position as an output of the monitoring system, for example, providing a clinician with a continuous output.

In some examples, such a position estimate is determined as part of a multiple dipole modeling approach for extracting the fECG signal from the raw signals that include both fetal and maternal signals, in which estimated orientation of the dipole of the fetal heart provides an estimate of the orientation of the fetus relative to the mother's body.

In some examples, the fetal position is used as part of the feature extraction procedure, or as part of the clinical evaluation procedure. For example, signal acquisition in certain fetal positions may result in characteristically distinct signals, for example, that exhibit higher signal-to-noise characteristics. In some examples, automated clinical determinations are made as a function of the fetal position, for example, being performed only in certain fetal positions. An example of such a fetal position is a fetus with its back to the maternal abdominal wall, which may result in particularly high quality signals due to the short distance between the fetal heart and the surface electrodes. In some examples, the estimated fetal position is used to select electrodes in the channel selection module 140. In some examples, the estimated fetal position is used to determine signal and/or model characteristics related to various electrodes, for example, to determine signal transmission characteristics between the signal source (e.g., fetal heart) and the electrodes.

Other examples of analyzing modules implemented in the ECG analyzer 250 include a heart rate tracker 258, a fetal ECG waveform extractor (not shown), and possibly other modules that associate user-determined statistics with clinical analysis. The heart rate tracker 258 may provide a continuous output of fetal heart beat over time and automatically identify the occurrence of heart rate acceleration, deceleration, and certain types of irregularity that can be early manifestation of serious medical conditions such as cardiac arrhythmia.

Note that the pre-processor 250 may provide signals to various analyzing modules in different forms. In other words, the input data to the clinical condition detector 252 is not necessarily the same data provided to the orientation detector 256 or the heart rate tracker 258. Depending on the particular implementation, some analyzing modules may accept data representing "clean" fetal ECG waveforms, whereas others may accept data representing metrics of predefined fetal-maternal ECG models.

Figure 4:
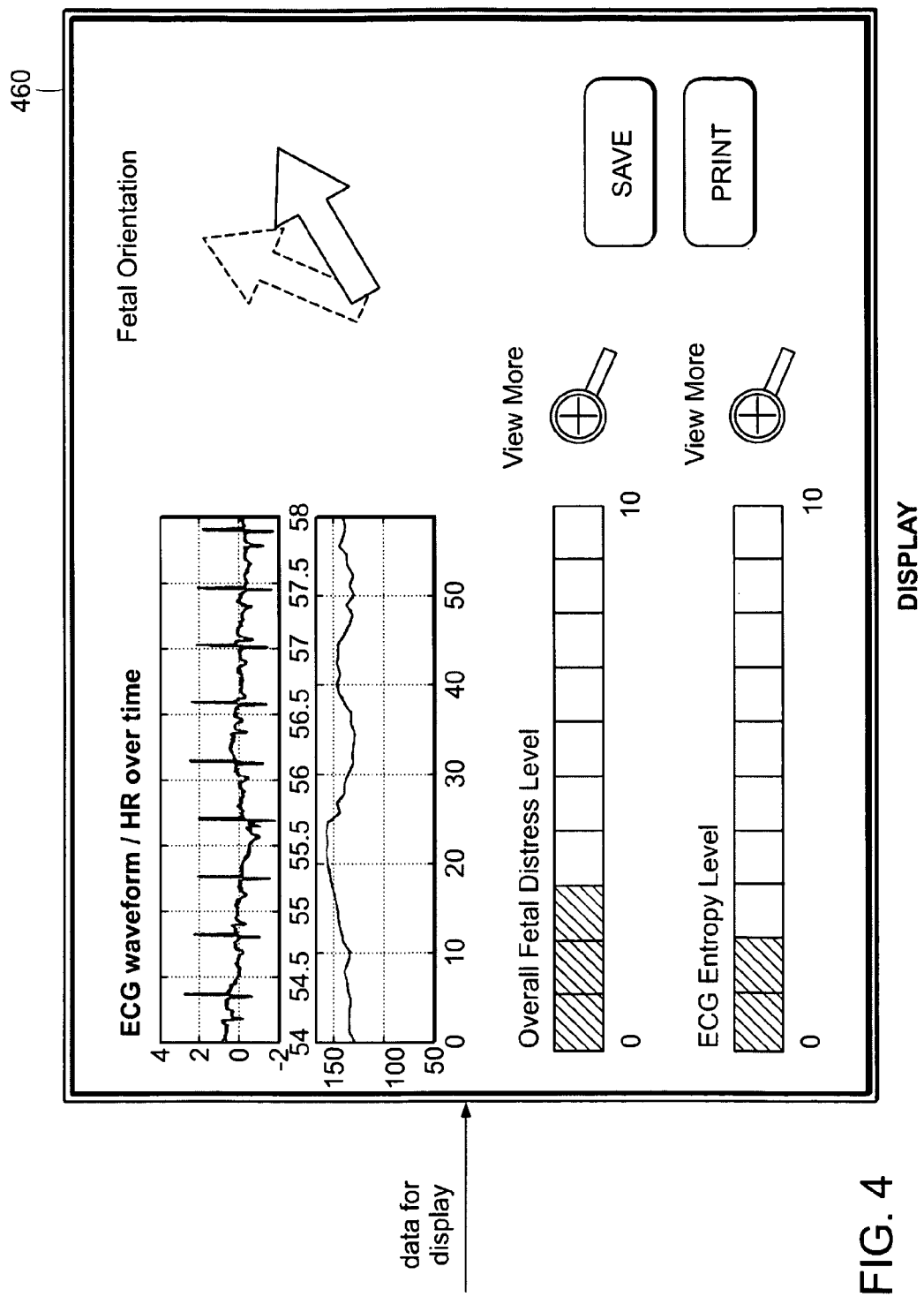
FIG. 4 shows an example of data display of the fetal monitoring system of FIG. 1.

FIG. 4 shows one example of a data display by which the outputs of various analyzing modules are presented to physicians, for example, on a computer screen or a handheld device. This display includes multiple regions that respectively show, for example, a fetal ECG waveform along with observed fetal heart rate, a fetal orientation pointer, an overall fetal distress index, an entropy index, and possibly other indices. In some examples, changes in fetal position since the most recent examination (or over the entire course of pregnancy) are also presented, for example, by loading prior position data from a patient database. In some examples, each index has a predefined "alert" level (e.g., a score of 6 out of 10) beyond which special attention (e.g., follow-up procedures) is indicated. In some examples, the monitoring system 100 also allows physicians to view detailed data, for example, the statistics upon which a particular index value is determined, when there is a need.

2 Electrode Configuration

Depending on the particular implementation, ECG signals can be collected using invasive and/or non-invasive approaches with the electrodes 132 placed in a variety of arrangements. The following description provides two examples of electrode configurations suitable for use with the monitoring system 100 of FIG. 1.

2.1 Example I

Figure 5:
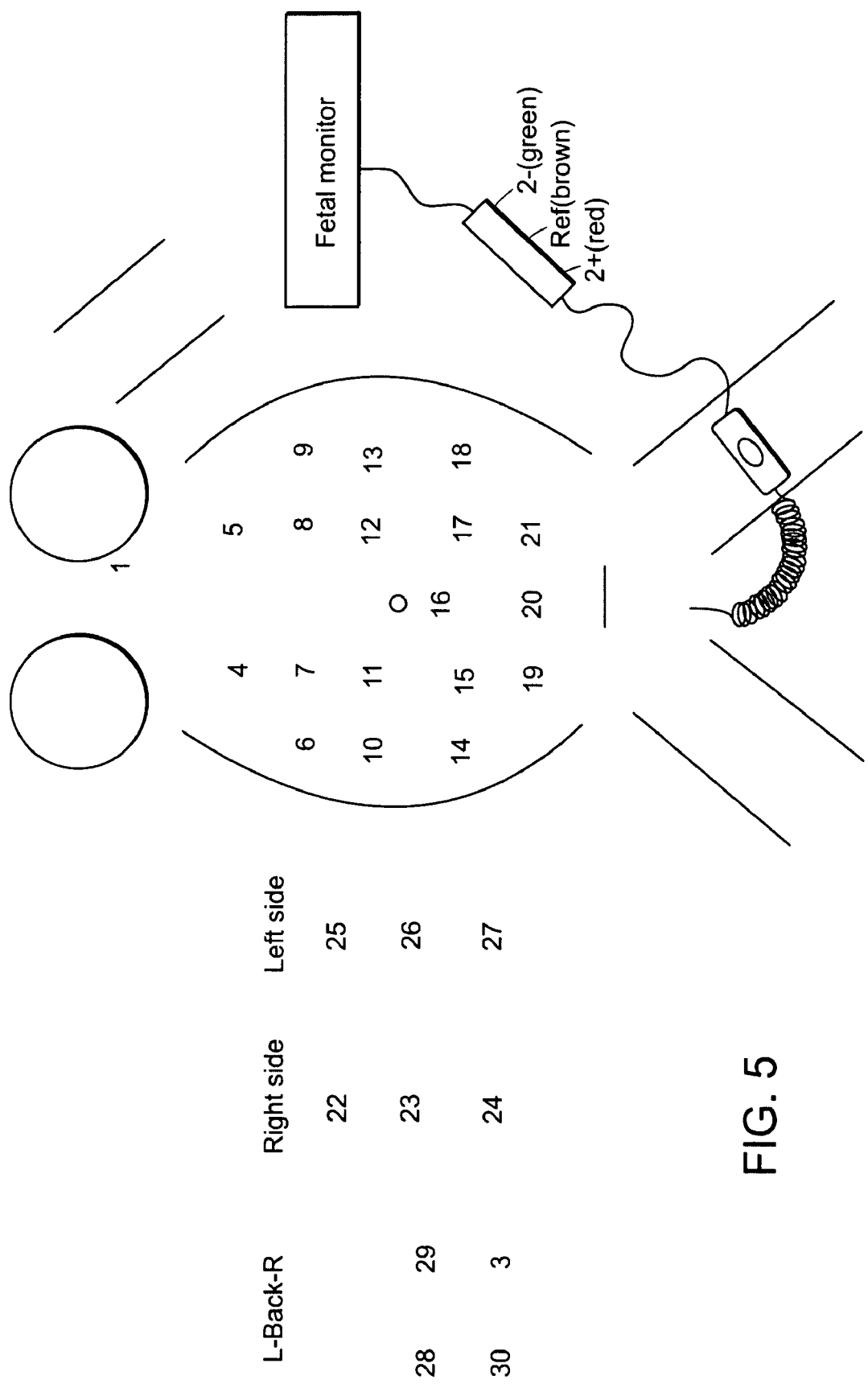
FIG. 5 shows one example of electrode configuration.

Referring to FIG. 5, a first electrode configuration of some embodiments of the data acquisition system 130 is shown. In this example, the configuration is capable of simultaneously collecting fetal scalp electrode ECG data ("gold-standard" fetal data), maternal ECG data ("gold-standard" maternal data), and combined data (fetal-maternal mixture) from the maternal abdomen. Fetal ECG data can be isolated from the combined data using the gold standard maternal data and can be further compared with the gold standard fetal data.

In this example, ECG signals are obtained using 32 adhesive electrodes, including: 3 maternal chest electrodes (producing a robust maternal gold standard reference), 28 abdominal and back electrodes (producing an over-complete set of maternal/fetal mixtures), and a fetal single scalp electrode inserted using an intra-uterine probe. The single intra-uterine probe, although not employed without indication, can be optionally used on a significant number of patients (e.g., in-labor patients). This probe can provide a strong, low-noise, fetal ECG signal, and hence a "gold standard" with which to compare the extracted fetal ECG from the abdominal probes. The three chest electrodes provide a strong maternal ECG representation with no (or negligible) fetal contamination. Using the chest and scalp electrodes, the quality of both the maternal removal and the fetal extraction can be evaluated. Depending on implementation, these electrodes can either be dry electrodes (e.g., Orbital Research, Cleveland, Ohio) or commercial gel adhesive electrodes (e.g., Red Dot, 3M, St. Paul, Minn.). In some examples, the electrodes are mounted onto the maternal body using a mesh (or garment), which can stabilize electrodes and improve electrode-skin contact during examination.

Figure 6:
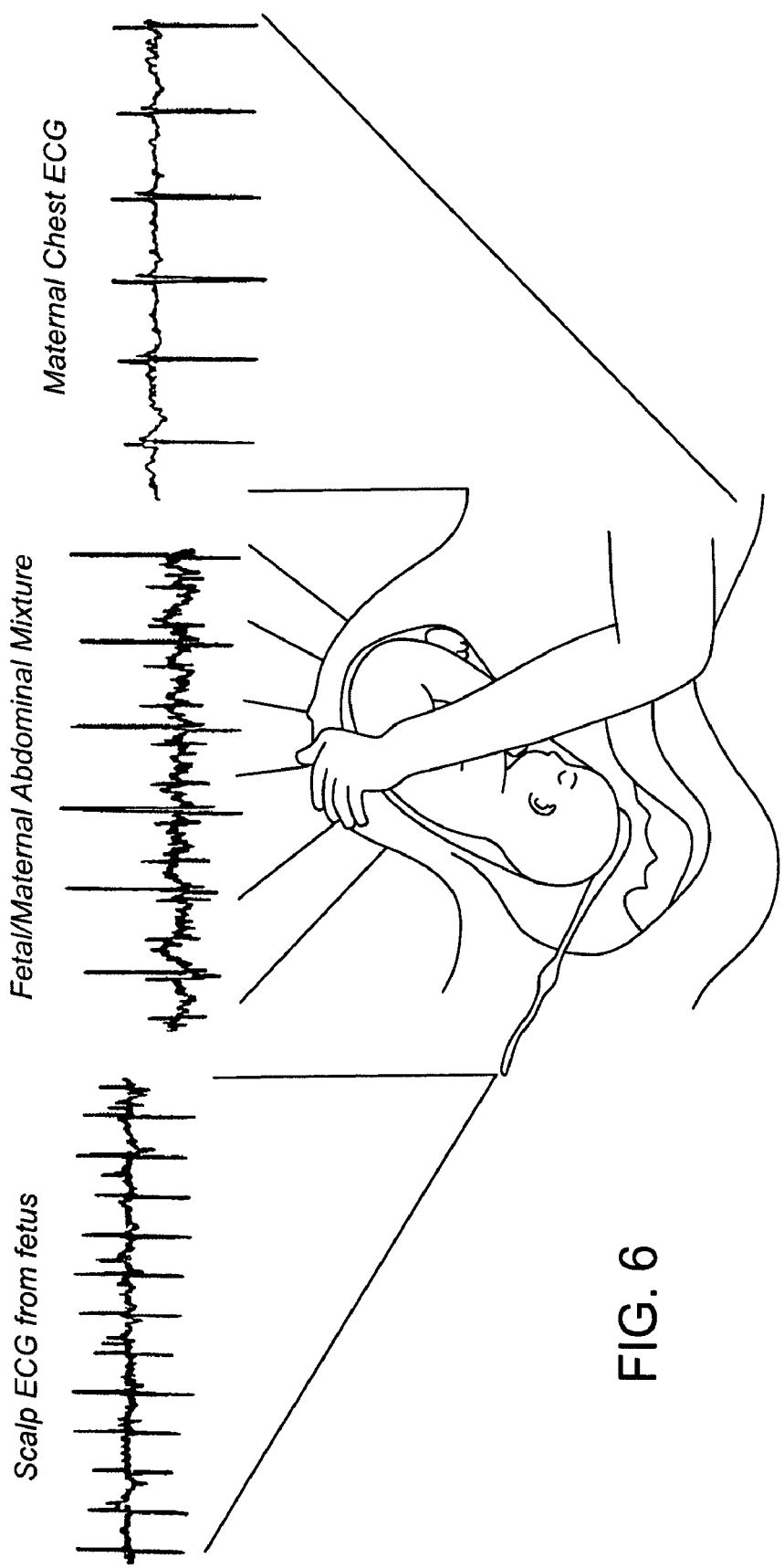
FIG. 6 shows ECG waveforms collected using the electrode configuration of FIG. 5.

FIG. 6 shows exemplary ECG waveforms detected using the above described data acquisition system. These waveforms include fetal ECG, fetal-maternal ECG, and maternal ECG obtained respectively from fetal scalp electrodes, abdominal electrodes, and chest electrodes.

2.2 Example II

Referring to FIG. 7, a second electrode configuration of some embodiments of the data acquisition system 130 is shown. Here, a set of dry electrodes (e.g., 32) are mounted on a convenient elastic monitoring garment that is strapped around the maternal abdomen to allow the electrodes to be distributed in a predetermined arrangement over the abdomen, the back, and on the sides of the patient. No fetal scalp electrode is necessary with this configuration. This configuration provides a non-invasive means to monitor fECG signals yet still capable of providing a sufficient set of useful fECG signals regardless of the fetal status.

In some embodiments, the electrode arrangement and the lead pattern by which electrical signals are collected can use conventional standards developed on adult patients. One example of such a conventional standard makes use of a well-established 12-lead pattern, with each lead recording the electrical activity of the adult heart from a different perspective. The signal of each lead can correlate with a different anatomical area of the heart, for example, to help identify acute coronary ischemia or injury. Fetal ECG signals are contained in some or all of the lead signals and may be extracted using various data extraction and filtering methods (as will be described later). In some cases, the isolation of fetal signals from fetal-maternal mixtures can be difficult as the conventional standards were developed based on adult models without accounting for the influence of fetal presence and the resulting fetal-maternal mixtures can be either poorly characterized or contain very low fetal components relative to the predominant maternal signals.

In some other embodiments, the electrode arrangement and the lead pattern use a design that suits the particular need of fetal ECG monitoring. One example of the design is shown in FIG. 7, which illustrates the placement of some electrodes in a side view, a back view, and a sectional view of the patient body. In this example, the entire set of electrodes forms at least of a group of cross-body leads each of which generates electrical signals along an imaginary line across the body, for example, from back to front, or from left side to right side. Some of these leads are each formed by a respective pair of electrodes, one being referred to as a collecting/positive electrode (e.g., E1) and the other being referred to as a reference/negative electrode (e.g., R1). The corresponding lead signal (e.g., L1) is obtained, for example, using a biomedical instrumentation amplifier that forms an amplified signal representing a voltage differential between the collecting electrode and the reference electrode. For some of these leads, the reference electrode is placed at the opposite side of the body to which the collecting electrode is attached. For example, some of the collecting electrodes are placed in the abdominal region while the corresponding reference electrode(s) are placed in the lumbar region. Similarly, some of the collecting electrodes can be placed in the left side of the body while the corresponding reference electrode(s) are placed in the right side of the body.

Using such a lead pattern, some of the collected signals can exhibit a stronger fetal component and/or contain less noise compared with lead signals collected using conventional adult standards. Depending on the particular implementation, each lead does not necessarily use a different electrode. In other words, some leads may be formed using collecting electrodes at various positions in the abdominal region against a single reference electrode in the lumbar region. In some examples, the reference electrodes and the collecting electrodes can be electrodes of different characteristics (for example, made from different materials, having different sixes, and/or exhibiting different levels of signal sensitivity) and be attached to the body using different attachment mechanisms (e.g., dry vs. wet). In some examples the set of electrodes is couples to a lead reconfiguration module that can dynamically adjust electrode pairing, lead selection, and/or garment positioning based on feedback signals provided by the ECG analyzer 150 to account for, for example, fetal position changes, loss of electrode contact, and other events that may cause abrupt changes in certain electrode or lead signals.

3 Channel Selection

In the exemplary electrode configurations shown in FIGS. 5 and 7, one reason to record a large number of abdominal and back signals described above is that the fetal ECG tends to manifest in only a subset of these leads, yet the actual combination is dependent on the state of the fetus, the time through pregnancy, the degree of electrical contact, and the location and orientation of the fetus or fetuses. Therefore, the channel selection module 140 is configured to adaptively select channels of "strong" (high quality) signals and discards channels of "weak" signals. As some of the abdominal signals will contain primarily noise, preferably, these channels are discarded from processing.

One technique used by the channel selection unit 140 to select channels of useful signals is based on fusing multiple signal quality indices (SQI) derived from multiple ECG leads. In some examples, physiological SQIs are obtained by analyzing the statistical characteristics of each channel and their relationships to each other. For instance, by computing spectral coherence, statistical departures from Gaussianity, and the performance of differently-sensitive event detectors, this technique allows the automatic location of channels that contain useful signal, and discarding of those that contain primarily noise. Furthermore, a sliding scale of quality is available to enable the selection of different channels for different applications. Further discussion of this technique is provided by Li et al., in "*Robust Heart Rate Estimation from Multiple Asynchronous Noisy Sources Using Signal Quality Indices and a Kalman Filter*," published in Physiological Measurement 29 (2008) 15-32, the disclosure of which is incorporated herein by reference.

4 Extraction of Fetal Signals from Fetal-Maternal Mixtures

Some techniques to extract waveforms of fetal ECG signals from the fetal-maternal mixtures include signal processing and filtering techniques such as adaptive filtering (AF), nonlinear projective filtering (NLPF), neural networks, independent component analysis (ICA) and joint time-frequency analysis (JTFA). One limitation of these techniques lies in their dependencies on the signal-to-noise ratio (SNR) of the data and sensitivity to the frequent artifacts that manifest during fECG acquisition. Each technique may either perform an "in-band" filtering (removing frequency signals that are present in the fetal signal) or produce a phase distortion in the signal that has an unknown affect on the fECG morphology. These issues may result in significant changes in the clinical parameters one wishes to extract from the fECG.

Another issue in fetal ECG recording and analysis deals with signal distortions that result from the transmission of the fetal signal trough the mother's abdomen. To reach the surface electrodes, fECG signals pass through multiple layers of media (e.g., the vernix caseosa) each of which may have very different electric properties and some may cause significant attenuation the fetal ECG signals collected from surface electrodes. Since the effective frequency range of the ECG is below 1-2 KHz and considering the distance between the body surface electrodes and the cardiac sources, the propagation medium of the maternal body may be considered as a linear instantaneous medium. The body surface recordings are hence a linear instantaneous projection of the cardiac sources and artifacts onto the axes of the recording electrode pairs. It is however known that the electrical impedance of the body volume conductor changes with respiration. Therefore despite its linearity, the propagation medium is time-varying and the body surface recordings are rather non-stationary.

One method to address the issue of fetal ECG distortion due to transmission through media of varying dielectric constants is to use a model of the fetal cardiac source to constrain the filtering and feature extraction process. One technique, for example, applies a three-dimensional dynamic model to represent the electrical activity of the heart. More specifically, this model is based on a single dipole model of the heart and is later related to the body surface potentials through a linear model which accounts for the temporal movements and rotations of the cardiac dipole, together with a realistic ECG noise model. Details of this technique are further described by Sameni et al., in "*Multichannel ECG and Noise Modeling: Application to Maternal and Fetal ECG Signals*," published in EURASIP Journal on Advances in Signal Processing, Volume 2007, Article ID 43407, the disclosure of which is incorporated herein by reference.

FIG. 8A illustrates a typical mixture of maternal and fetal ECG. The maternal beats appear as negative spikes (HR=90 bpm), and the fetal beats appear as the smaller, positive spikes (HR=138 bpm). Both the fetal and maternal peak heights appear to be modulated by some low-frequency component (including, e.g., respiration). A fetus will "practice" respiration prior to birth, and this can lead to changes in intrathoracic pressure.

FIG. 8B illustrates the same signal after maternal subtraction using a model-based Kalman Filter tracking method described above. Note that the respiratory-modulation of the R-peaks and other features of the fECG are preserved in the waveform. These subtle features are essential in performing accurate feature analysis, such as R-peak location (e.g., for heart rate variability evaluation of sepsis), ST-elevation analysis (e.g., for ischemia) and QT interval analysis (for pro-arrhythmic indications).

Using these "clean" fetal ECG waveforms, the feature extractor 253 of FIG. 2 is able to identify characteristics of the waveforms that are associated with clinically relevant activities. Examples of ECG characteristics include heart rate variability, ECG morphology, and entropy. For instance, fECG signals may be grouped into different morphological classes, and each class may be further divided based on subtle morphological characteristics, based on which patterns of clinical relevance may be identified. Techniques of feature extraction are described in greater detail below in the following sections.

In some examples, the feature extractor 253 does not need the "clean" fetal ECG waveforms in order to obtain features of interest. For instance, the pre-processor 251 may process the raw ECG data to obtain metrics of ECG models or symbolization of ECG classification, based on which the feature extractor 150 may extract interesting features.

5 Feature Extraction and Clinical Analysis

5.1 Heart Rate Variability Analysis

Heart rate variability (HRV) can be an important quantitative marker of cardiovascular regulation by the autonomic nervous system. Heart rate is generated by the intrinsic rhythm of the sinoatrial node in the heart, but constant input from the brainstem through a feedback loop in the autonomic nervous system closely modulates this rate. At rest, variation in heart rate arises predominantly from vagal tone governed by the vagus nerve nuclei. However, this variation is affected by the interaction between vagal and sympathetic activity, as well as by central respiratory and motor centers and peripheral oscillations in blood pressure and respiration.

In many clinical settings, evaluation of HRV is based on the subjective interpretation of this variable by clinicians using paper printouts that plot the fetal heart rate as a function of time. In some embodiments, heart beat may be detected by cross-correlating the cardiac signal with a reference heart beat trace from data recorded using the fetal ECG. The height of the cross-correlation peak (if it is not normalized) provides a measure of the strength of the signal and its similarity to the reference. The position of the peak provided an accurate measure of the exact time the beat occurred. These measures provided a way to reject signal that is not a fetal beat as well as to measure accurately the time between beats (the fetal heart rate). This approach provides data that can be used for analyses based on rate and HRV.

The cross-correlation can be used to locate fetal heart beats in the data, which can then be "windowed" out into a series of individual heart beats. The data is then subjected to a multivariate statistical analysis, and the results are used to group beats according to variations in the ensemble of heart beats. These data can be later used for the analysis of waveform morphology.

5.2 Morphological Analysis

In some embodiments, the feature extractor 253 performs morphological analysis on the fECG signal. One approach to analyzing fetal ECG morphology uses clustering and symbolic analysis of ECG signals to discover medically relevant patterns. Very generally, ECG signals are classified into groupings that are morphologically similar according to a signal waveform similarity measure. In some examples, successive segments of the fECG waveform are formed with one segment per beat, and min-max clustering is then used to form the groupings according to pair-wise distance between the waveform segments. In some embodiments, the pair-wise distance between segments uses a dynamic time-warping (DTW) measure. In other examples, each segment is modeled using a parametric model (e.g., using a sum of displaced Gaussian components) and the distance between segments is based on a distance between the model parameters of the segments. The characteristics of the identified groups are used to determine a measure of morphological variation. In some examples, the segments of the fECG are labeled, for example, with discrete labels from an alphabet of symbols (e.g., 5 arbitrary labels). Then a statistical measure is determined from the sequence of labels, for example, in a sliding window of the signal.

One measure of morphological variation is an entropy of a sample distribution of the labels. In some examples, the entropy of a finite state model of the sequence is used. In some examples, the segments are not necessarily deterministically labeled (relying on a probability measure for beats in each hidden class), and the entropy of a underlying (e.g., hidden) sequence of segment classes is computed, thereby avoiding a need to first determine an accurate series of class labels, which may require a "clean" estimate of the fECG signal. Some aspects of these approaches are described by Syed et al., in "*Clustering and Symbolic Analysis of Cardiovascular Signals: Discovery and Visualization of Medically Relevant Patterns in Long-Term Data Using Limited Prior Knowledge*," published in EURASIP Journal on Advances in Signal Processing, Volume 2007, Article ID 67938, the disclosure of which is incorporated herein by reference.

Unlike the techniques incorporated into ECG monitors and ICU monitoring devices that compare observed phenomena to standardized patterns representing pathophysiological conditions (ventricular tachycardia or ST-depression, for example), some entropy-based approaches of the types described above do not necessarily assume a priori information about the ECG morphology. Each morphological class is represented by a symbol, and various patterns of symbols in sequence may have clinical significance. This analytic approach is suited for the fetal ECG data collected in the present system 100, because with the exception of ST-segment analysis, there are no formal systems for fetal ECG evaluation. Independence from a priori information can be useful in fetal applications where the information may not be available, or may be highly variable based on factors such as fetal age.

In some examples, model-based filtering is applied to the fECG signal, for example, prior to entropy-based analysis. For example, Gaussian based modeling as described in Clifford et al., "Model-based filtering, compression and classification of ECG," *International Journal of Bioelectromagnetism* Vol. 7, No. 1, pp 158-161, 2005, and in U.S. Patent Publication 2007/0260151, "Method and Device for Filtering, Segmenting, Compressing and Classifying Oscillatory Signals," published Nov. 8, 2007, are used in processing the fECG signals. These references are incorporated herein by reference. In some examples, the classification based on these techniques is used in determining entropy measures as described in the Syed reference. For example, each class may be characterized by a range of model parameters for that class (e.g., by partitioning the space of parameters values) or each class be associated with a distribution of the model parameters for that class.

6 Examples of Clinical Applications

In some embodiments, characteristics of ECG patterns are associated with events of clinical activity. Some examples of such clinical applications includes using an entropy measure of a fECG signal as an indicator of an inflammation condition, or as an indicator of a cause of an inflammation condition, for example, an infection-based cause of inflammation.

In an experimental application of signal processing and analysis techniques described above, the fECG waveforms of 30 recordings discovered a change in the morphology of the heart beat that occurs prior to the development of chorioamnionitis.

Figure 9A:
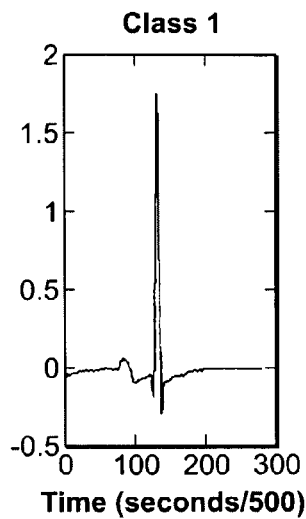
FIGS. 9A-9C show three exemplary classes of ECG waveforms, respectively.
Figure 9B:
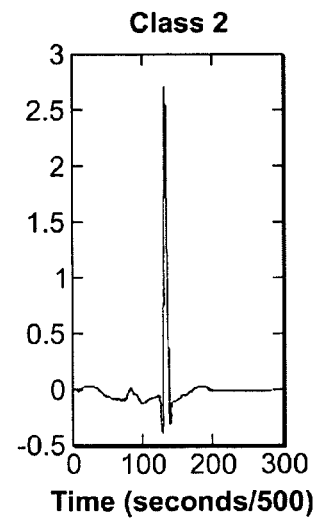
Figure 9C:
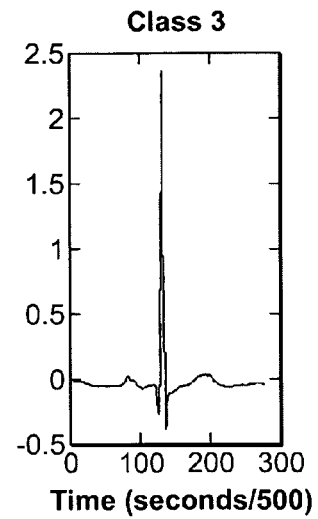
Figure 9D:
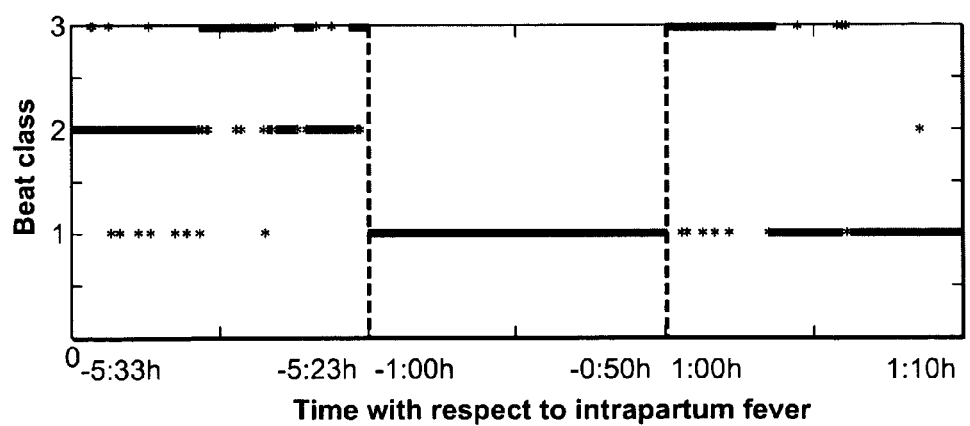
FIG. 9D shows the occurrence of different classes of ECG waveforms in one patient with respect to time.

FIGS. 9A-9C illustrate three classes of QRS complexes classified from a 7-hour dataset collected from a woman who developed chorioamnionitis during labor. FIG. 9D shows the occurrence of each beat during 10-minute intervals timed with respect to the onset of maternal fever of the same patient. Note the consistent appearance of class 1 ECG signals one hour prior to the development of fever.

Analyses of the fetal ECG waveforms also show that a measure of entropy—the degree of disorder in the similarity of the morphology of sequences the fetal heart beats—distinguishes those fetuses subject to intra-amniotic infection from those without exposure to infection.

Figure 10B:
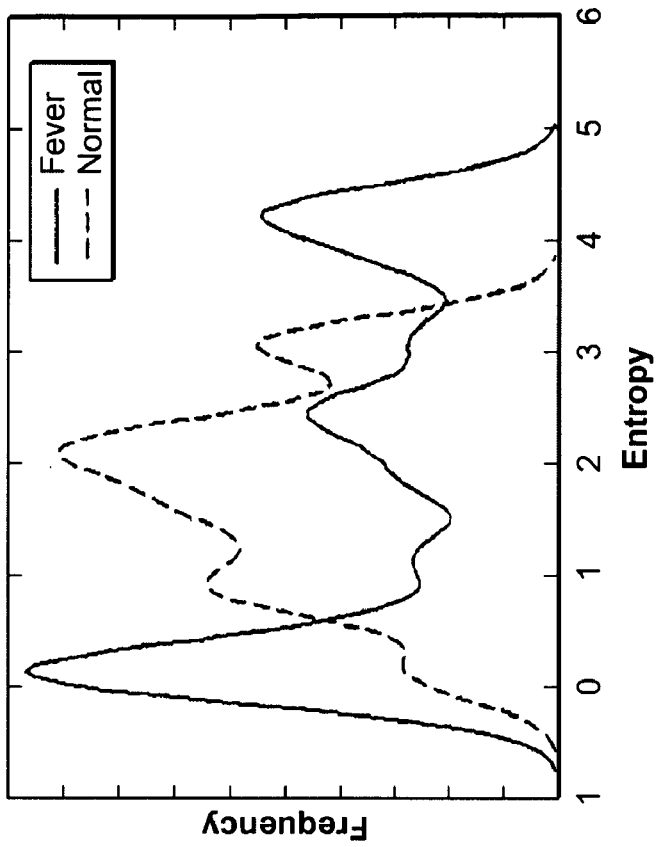
FIG. 10B illustrates the distribution of ECG entropy among fever and normal populations.
Figure 10A:
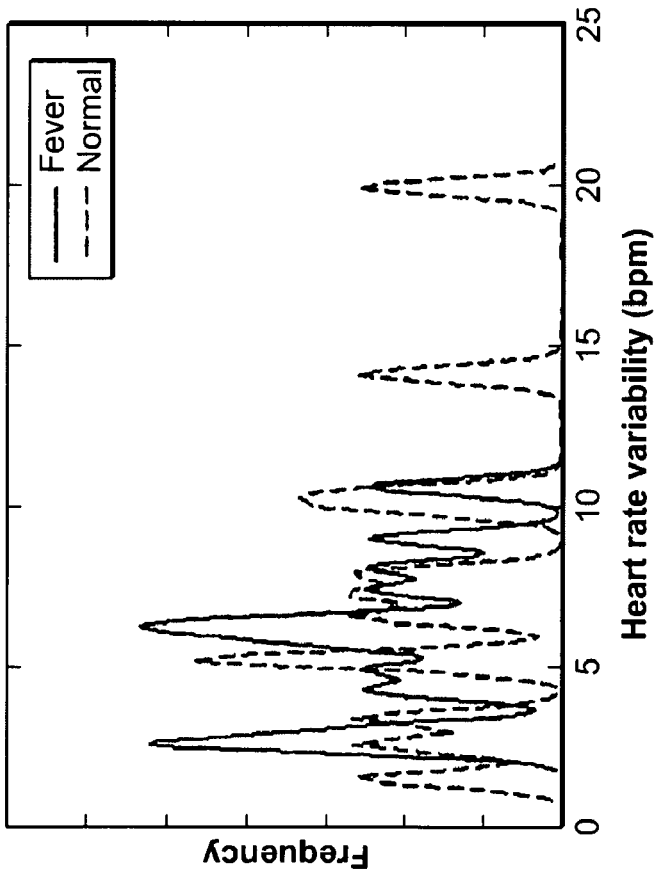
FIG. 10A illustrates the distribution of heart rate variability among fever and normal populations.

FIGS. 10A and 10B illustrate respectively the HRV analysis and entropy analysis of 30 fetal ECG datasets from women with chorioamnionitis and women without infection. As shown in FIG. 10A, the distribution of fetal HRV for fetuses subjected to chorioamnionitis (e.g., exhibiting maternal fever symptom) is not easily distinguishable from that of fetuses in an uninfected intrauterine environment. In comparison, FIG. 10B shows that, when the entropy of the fetal ECG signal is calculated for the same set of fetal ECG data, fetuses subjected to chorioamnionitis are bimodally distributed with respect to entropy, whereas fetuses in an uninfected environment are essentially normally distributed. In other words, an ECG waveform having a very low (e.g., 0) or very high (e.g., 4) entropy indicates a higher probability of developing chorioamnionitis. In some examples, the distributions of observed entropy measures in two known classes of patients (e.g., condition present versus normal) are used to form a likelihood ratio test to classify a patient based on an observed entropy.

In some examples, different patterns of electrophysiological behaviors can be correlated with medical conditions using specific biochemical markers of such conditions, e.g., markers of inflammation and brain injury measured from fetal umbilical cord collected from the patient. Umbilical cord blood interleukin-6, for example, is significantly elevated in fetuses that develop sepsis compared with fetuses that do not develop sepsis. Cord blood levels of IL-6 greater than 108.5 pg/ml are considered 95% sensitive and 100% specific for neonatal sepsis.

Figure 11:
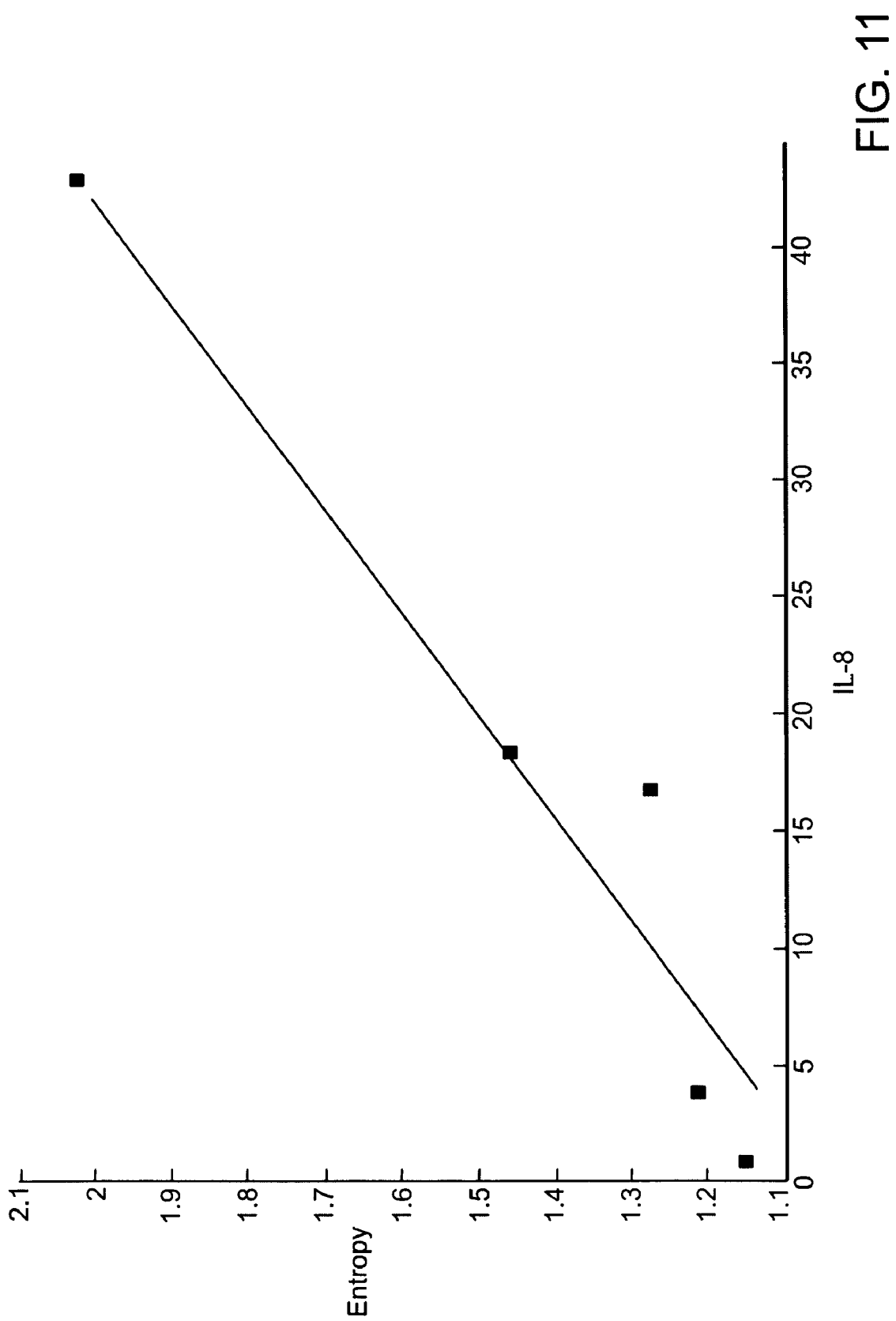
FIG. 11 illustrates a correlation between ECG entropy and IL-8 level.

FIG. 11 shows an association between the morphologic entropy of the fetal ECG and fetal umbilical cord serum interleukin-8 (IL-8) levels. Increasing levels of IL-8 are correlated (e.g., having a substantially linear relationship) with increasing disorder in the fetal ECG morphology. One possible explanation of this correlation is that an in-utero fetal inflammation/infection is associated with quantitative changes in the fetal ECG, reflecting altered electrophysiological signaling at the level of the fetal brainstem, fetal myocardium, or both.

Another related application relates to using characteristics of ECG signals to discriminate between different possible causes of medical conditions. Various causes of diseases may induce changes in ECG morphology through different mechanisms, which may in turn lead to distinguishable patterns in ECG morphologies. For example, infection, which is one explanation for inflammation, may induce a morphological change in fetal ECG signals through brain stem and myocardium level; while preeclampsia (pregnancy-induced hypertension) is likely to affect the ECG morphologies through mechanism of placental failure. The various presentations of ECG morphologies can therefore be used as a basis for discriminating between different causes of certain diseases.

In some embodiments, the feature extractor 253 performs signal analysis that is not necessarily related to ECG signals. For example, muscle signals are detected using the surface electrodes or conventional pressure sensors for contractions, and timing and intensity of uterine contractions are estimated. This approach has an advantage of providing a single monitoring device being applied to the mother, while providing multiple clinically-relevant signals.

In some embodiments, the fetal monitoring system 100 may incorporate functions of other medical diagnostic tools to enhance fetal ECG detection and/or assist clinical evaluations. For example, a maternal reference signal can be obtained using other sensing modes, such as ultrasound, imaging, and blood pressure sensing, to facilitate fetal ECG extraction. Also, histological and pathological data of a patient can be assessed in conjunction with ECG data to detect inflammation and neuronal injury before the onset of permanent disability.

It is to be understood that the foregoing description is intended to illustrate and not to limit the scope of the invention, which is defined by the scope of the appended claims. Other embodiments are within the scope of the following claims.

What is claimed is:

1. A method for fetal monitoring comprising:
    acquiring electrical signals from a plurality of electrodes, including a plurality of electrodes applied to a maternal abdominal region;
    analyzing the electrical signals, including performing a morphological analysis of fetal electrocardiogram signals;
    determining a clinical indicator of a pathologic condition from a result of performing the morphological analysis.

2. The method of claim 1 wherein performing the morphological analysis includes determining a quantitative measure of morphological variation.

3. The method of claim 2 wherein determining the quantitative measure of morphological variation includes characterizing segments of signals determined from the acquired electrical signals according to a group of classes, and determining a measure of variation in sequences of segment classifications.

4. The method of claim 2 wherein the quantitative measure of morphological variation includes an entropy of a sequence of segment classifications.

5. The method of claim 1 wherein determining a clinical indicator includes determining an indicator of a fetal condition.

6. The method of claim 1 wherein determining a clinical indicator includes determining an indicator of an inflammation condition.

7. The method of claim 1 wherein determining a clinical indicator includes determining an indicator of at least one of chorioamnionitis, preeclampsia, inflammation, and infection.

8. A fetal monitoring system comprising:
    a data acquisition system for acquiring surface signals including signals representing surface measurements of cardiac activity;
    a signal analyzer coupled to the data acquisition system, configured to analyze the acquired surface signals to generate an output having at least a clinical indicator characterizing a pathologic condition, the signal analyzer including:
        a signal processor for extracting fetal electrocardiogram signals from the acquired surface signals; and
        a clinical condition detector configured to perform a morphological analysis of the extracted fetal electrocardiogram signals, and based on a result of the morphological analysis, determining the clinical indicator; and
    an output system for presenting a representation of the clinical indicator.

9. The fetal monitoring system of claim 8, wherein the data acquisition system includes an electrode array having at least a plurality of electrodes attachable to a maternal abdominal region.

10. The fetal monitoring system of claim 9, wherein the electrode array further includes a second plurality of electrodes attachable to a maternal lumbar region.

11. The fetal monitoring system claim 10, wherein the electrode array further includes a third plurality of electrodes attachable to a maternal side region.

12. The fetal monitoring system of claim 11, wherein the pluralities of electrodes are positioned in a pre-determined arrangement on a garment.

13. The fetal monitoring system of claim 8, wherein the output system includes a display unit for generating a visual representation of the output of the signal analyzer.

14. The fetal monitoring system of claim 13, wherein the display unit includes a computer screen.

15. The fetal monitoring system of claim 13, wherein the display unit includes a handheld device.

16. The fetal monitoring system of claim 15, further comprising a wireless transmitter for transmitting the output of the signal analyzer to the handheld device.

17. The fetal monitoring system of claim 8, wherein the signal analyzer further includes a heart rate detector for determining a fetal heart rate from the acquired surface signals.

18. The fetal monitoring system of claim 17, wherein the output system is further configured for presenting a representation of the fetal heart rate determined by the signal analyzer.

19. The fetal monitoring system of claim 17, wherein the heart rate detector is further configured for determining a degree of irregularity in the fetal heart rate.

20. The fetal monitoring system of claim 8, wherein the clinical condition detector is further configured for determining a measure of morphological variation in the extracted fetal electrocardiogram signals.

21. The fetal monitoring system of claim 20, wherein the measure of morphological variation includes an entropy of a sequence of segment classifications.

22. The fetal monitoring system of claim 8, wherein the clinical indicator determined by the clinical condition detector includes an indicator of a fetal condition.

23. The fetal monitoring system of claim 8, wherein the clinical indicator determined by the clinical condition detector includes an indicator of at least one pathologic condition from the group consisting of chorioamnionitis, preeclampsia, inflammation, infection, hypoxia, hypoxemia, and metabolic acidosis.

24. The fetal monitoring system of claim 8, wherein the output system is further configured for presenting a waveform representation of the fetal electrocardiogram signals.

25. The fetal monitoring system of claim 8, further comprising a signal selection unit coupled to the signal analyzer for selectively rejecting one or more of the acquired signals based on a quality of the acquired surface signals.

26. The system of claim 8 wherein the signal processor for extracting fetal electrocardiogram signals is configured to a) remove noise, b) remove artifacts, c) separate maternal signals, d) determine maternal heart rate, and e) determine fetal heart rate.

27. The system of claim 8 wherein the data acquisition module includes a signal conditioning module for filtering out undesirable noise and amplification.

28. The system of claim 27 wherein the data acquisition module further includes a digitization module for conversion at a sampling rate of 1000 samples per second and a resolution of 16 bits.

\* \* \* \* \*